United States Patent [19]

Fernandez et al.

[11] Patent Number: 4,904,686

[45] Date of Patent: Feb. 27, 1990

[54] ORGANIC COMPOUNDS AND THEIR USE AS PHARMACEUTICALS

[75] Inventors: Maria I. F. Fernandez, Madrid, Spain; Terrence M. Hotten, Farnborough; David E. Tupper, Reading, both of England

[73] Assignee: Lilly Industries Limited, Basingstoke, England

[21] Appl. No.: 179,601

[22] Filed: Apr. 11, 1988

[30] Foreign Application Priority Data

Apr. 13, 1987 [GB] United Kingdom ............... 8708833

[51] Int. Cl.$^4$ ................. A61K 31/38; C07D 333/62
[52] U.S. Cl. ............................ 514/422; 514/317; 514/324; 514/326; 514/383; 514/385; 514/397; 514/402; 514/406; 514/443; 514/445; 540/466; 540/480; 546/202; 546/210; 546/211; 546/212; 546/213; 548/255; 548/262; 548/336; 548/374; 548/518; 548/525; 548/527; 549/52; 549/54; 549/55; 549/63; 549/64
[58] Field of Search ............... 549/64, 52, 54, 55, 549/63; 548/527, 255, 262, 336, 374, 518, 525; 546/212, 213, 202, 210, 211; 544/146, 379; 514/326, 422, 448, 317, 324, 383, 385, 397, 402, 406, 443, 445

[56] References Cited

U.S. PATENT DOCUMENTS 3,177,252 4/1965 Thominet .
3,342,826 9/1967 Miller et al. .
3,932,503 1/1976 Weber et al. .
4,123,550 10/1978 Untch et al. .
4,221,815 9/1980 Weyer et al. .
4,321,378 3/1982 Dostert et al. .
4,560,751 12/1985 Seybold .

FOREIGN PATENT DOCUMENTS 0065295 11/1982 European Pat. Off. .
60235 6/1986 European Pat. Off. .
1937759 9/1970 Fed. Rep. of Germany .

OTHER PUBLICATIONS

C.A. 72, 3226a (1970).
C.A. 67, 2167w (1967).
C.A. 101, 122562j (1984).
C.A. 100, 84964m (1984).
Consiglio et al., *J. Chem. Soc. Perkin Trans. II,* 1983, 1559-61.

*Primary Examiner*—Alan Siegel
*Attorney, Agent, or Firm*—Joseph A. Jones; Leroy Whitaker

[57] ABSTRACT

Compounds of the following formula have pharmacutical properties:

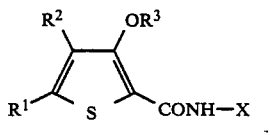

in which $R^1$ and $R^2$ independently are hydrogen, halo, nitro, amino, $C_{2-5}$ acylamino, $C_{1-4}$ alkyl, $C_{1-4}$ alkoxy, $C_{1-4}$ alkylthio, $C_{1-4}$ alkylsulphonyl, N-substituted heterocyclyl, optionally substituted phenyl, optionally substituted phenylthio, optionally substituted phenylsulphonyl or optionally substituted phenylsulphonamido, or $R^1$ and $R^2$ together form a $C_{3-5}$ alkylene bridge, $R^3$ is $C_{1-4}$ alkyl or $C_{2-4}$ alkenyl, and X is (i) —(CH$_2$)$_n$N(R$^4$)$_2$ where each $R^4$ independently is $C_{1-4}$ alkyl, $C_{2-4}$ alkenyl or optionally substituted $C_6H_5CH_2$—, and n is 1, 2 or 3, or (ii) a 5- to 8-membered alicyclic group containing one or two nitrogen atoms and directly attached to the amido nitrogen or attached by a $C_{1-3}$ alkylene chain; and salts thereof.

13 Claims, No Drawings

ORGANIC COMPOUNDS AND THEIR USE AS PHARMACEUTICALS

This invention relates to organic compounds, their preparation and use as pharmaceuticals.

The compounds of the invention are of the formula

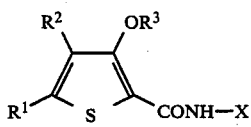 (I)

in which $R^1$ and $R^2$ independently are hydrogen, halo, nitro, amino, $C_{2-5}$ acylamino, $C_{1-4}$ alkyl, $C_{1-4}$ alkoxy, $C_{1-4}$ alkylthio, $C_{1-4}$ alkylsulphonyl, N-substituted heterocyclyl, optionally substituted phenyl, optionally substituted phenylthio, optionally substituted phenylsulphonyl or optionally substituted phenylsulphonamido, or $R^1$ and $R^2$ together form a $C_{3-5}$ alkylene bridge, $R^3$ is $C_{1-4}$ alkyl or $C_{2-4}$ alkenyl, and X is (i) $-(CH_2)_nN(R^4)_2$ where each $R^4$ independently is $C_{1-4}$ alkyl, $C_{2-4}$ alkenyl or optionally substituted $C_6H_5CH_2-$, and n is 1, 2 or 3, or (ii) a 5- to 8-membered alicyclic group containing one or two nitrogen atoms and directly attached to the amido nitrogen or attached by a $C_{1-3}$ alkylene chain; and salts thereof.

When X is an alicyclic group it is preferably attached at one of its carbon atoms and can contain an additional hetero atom as in a morpholino group or two nitrogen atoms as in piperazino, but preferably it contains only a single nitrogen atom. When the alicyclic group is attached via an alkylene chain, the chain is preferably of the form $-(CH_2)_n-$ where n is 1, 2 or 3 and X is thus of the formula $-(CH_2)_nY$ where Y is an alicyclic group attached at one of its carbon atoms.

The following are preferred examples of alicyclic groups:

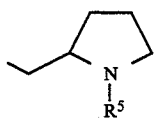

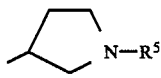

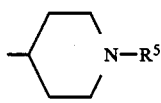

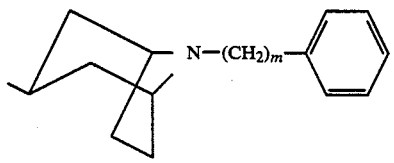

where m is 1, 2 or 3 and $R^5$ is $C_{1-4}$ alkyl, $C_{2-4}$ alkenyl or optionally substituted $C_6H_5CH_2-$.

The compounds of the invention and their pharmaceutically acceptable salts have useful effects on the central nervous system.

When $R^1$ or $R^2$, in the above formula, is halo it is preferably, fluoro, chloro or bromo and especially chloro or bromo. When reference is made to $C_{1-4}$ alkyl this includes, for example, methyl, ethyl, n-propyl, isopropyl and butyl and is especially methyl or ethyl. The groups $C_{1-4}$ alkoxy, $C_{1-4}$ alkylthio and $C_{1-4}$ alkylsulphonyl consist of these alkyl groups attached to the thiophene ring through an oxygen or sulphur atom or a sulphonyl group. The amino group is $-NH_2$ and the acylamino group of the formula RCONH— where R is preferably $C_{1-4}$ alkyl. When $R^1$ or $R^2$ is optionally substituted phenyl, optionally substituted phenylthio, optionally substituted phenylsulphonyl or optionally substituted phenylsulphonamido, it is preferably an unsubstituted phenyl, phenylthio, phenylsulphonyl and phenylsulphonamido group. If desired, however, the phenyl nucleus can be substituted with one or more, preferably one to three, substituents selected, for example, from halogen, $C_{1-4}$ alkyl, $C_{1-4}$ alkoxy, hydroxy, nitro, cyano, amino, carboxy and carboxamido. Examples of N-substituted heterocyclyl substituents are imidazolyl, pyrazolyl and triazolyl attached through a nitrogen atom, and in particular 1-pyrazolyl and 1-(1,2,4-triazolyl).

When $R^3$, $R^4$ or $R^5$ is $C_{2-4}$ alkenyl, it is preferably vinyl or propenyl, and when $R^4$ or $R^5$ is optionally substituted $C_6H_5CH_2-$, although preferably unsubstituted, it can be substituted on the phenyl group with, for example, one or more substituent as defined above for $R^1$ and $R^2$.

A preferred group of compounds is one in which X takes the value defined in (ii) above, that is, X is a 5- to 8-membered alicyclic group, and X is most preferably a group of the formula

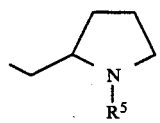

in which $R^5$ is $C_{1-4}$ alkyl, $C_{2-4}$ alkenyl or $C_6H_5CH_2-$.

The novel compounds of the invention are useful both as the free compound and as salts, for example the pharmaceutically-acceptable acid addition salts such as salts derived from non-toxic inorganic acids, for example, hydrochloric acid, nitric acid, phosphoric acid, sulphuric acid, hydrobromic acid, hydriodic acid and phosphorous acid, as well as salts derived from non-toxic organic acids such as aliphatic mono and dicarboxylic acids, especially fumaric acid, phenyl-substituted alkanoic acids, hydroxyalkanoic and hydroxyalkandioic acids, aromatic acids, aliphatic and aromatic sulphonic acids. In addition to pharmaceutically-acceptable salts, other salts are included such as, for example, those with picric or oxalic acids; they may serve as intermediates in the purification of the compounds or in the preparation of other, for example pharmaceutically-acceptable, acid addition salts, or are useful for identification, characterisation or purification of the bases.

It will be appreciated that the compounds of the invention can contain one or more assymetric carbon atom which gives rise to isomers. The compounds are normally prepared as racemic mixtures and can conveniently be used as such but individual isomers can be isolated by conventional techniques if so desired. Such racemic mixtures and individual optical isomers form part of the present invention and it is preferred to use an enantiomerically pure form.

Preferably the groups $R^1$ and $R^2$ are chosen from hydrogen, halogen, $C_{1-4}$ alkyl, $C_{1-4}$ alkoxy and $C_{1-4}$ alkylthio, and it is preferred that one of $R^1$ and $R^2$ is hydrogen or that both of $R^1$ and $R^2$ are $C_{1-4}$ alkyl. When one of $R^1$ and $R^2$ is hydrogen, it is preferably $R^2$. The group $R^3$ is preferably $C_{1-4}$ alkyl, especially methyl. Of the nitrogen-containing alicyclic groups the most preferred is that of the formula

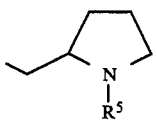

where $R^5$ is $C_{1-4}$ alkyl.

A preferred group of compounds according to the invention is of the formula

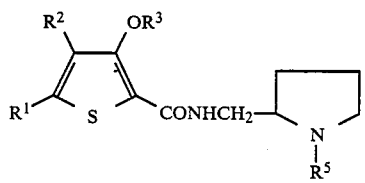

in which $R^1$ and $R^2$ independently are hydrogen, halo, $C_{1-4}$ alkyl, $C_{1-4}$ alkoxy or $C_{1-4}$ alkylthio, $R^3$ is $C_{1-4}$ alkyl, and $R^5$ is $C_{1-4}$ alkyl; and salts, especially the pharmaceutically-acceptable salts thereof. A most preferred group of compounds is one in which $R^1$ and $R^2$ are both the same or different $C_{1-4}$ alkyl. Such compounds have a chiral centre at the 2-position of the pyrrolidine ring and can thus exist in isomeric form and racemic mixtures. Generally the compounds are prepared as racemic mixtures whih can be separated into the individual enantiomers, or, alternatively the enantiomers can be prepared by utilising optically active amines in the preparation of the compounds. The preferred enantiomer is the laevorotatory (−) form.

The invention also includes a process for producing a compound according to formula (I) above, which comprises reacting a compound of the formula

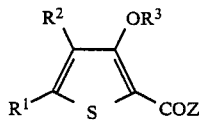 (II)

in which $R^1$, $R^2$ and $R^3$ have the values assigned them above, and Z is halo, —OH or —OR where R is a leaving group such as $C_{1-4}$ alkyl, with an amine of the formula

XNH$_2$ (III)

in which X has the above assigned values.

The reaction is preferably carried out at a temperature of from 0° C. to 200° C., more preferably from 0° C. to 100° C., in an inert organic solvent such as, for example a haloalkane, e.g. dichloromethane. When Z is —OH a coupling agent is preferably employed such as a coupling agent commonly used in peptide synthesis, for example carbonyldiimidazole. When Z is OR, it is often desirable to carry out the reaction at a higher temperature, for example from 100° C. to 200° C. The preferred reactions are those in which the reactant is one of formula (II) in which Z is halo or —OH.

Compounds of formula (II) are either readily available or can be prepared from known compounds by conventional synthesis. For example, the formula (II) compound can be prepared by alkylation of an intermediate of the formula

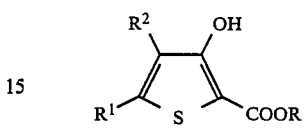

where R is hydrogen or $C_{1-4}$ alkyl, which can be synthesized by conventional methods as for example disclosed hereinafter.

The amine reactants of formula (III) are well known or are made by methods known in the art. For example, such cycloamine compounds are disclosed in J. Chem. Soc. (1957) 3165, South African Patent 69 00983, French Patent 2 534 255, and in Chemical Abstracts 66 2432g (1967), and the 2-amino-8-aza nortropane starting reactants are disclosed in French Patent 2 499 570.

As mentioned above, the compounds of the invention in free base and pharmaceutically acceptable acid addition salt form have useful central nervous system activity. The are also of low toxicity. Their activity has been demonstrated by testing in animal models using well-established procedures. More specifically, the compounds have been shown to block apomorphine induced climbing in mice according to the method of Costall, Naylor and Nohria (European J. Pharmacol. 50, 39; 1978), and/or to block a conditioned avoidance response in rats according to the method of Jacobsen and Sonne (Acta Pharmacol. et Toxacol. 11, 35, 1955), at doses below 50 mg/kg when administered intraperitoneally. For example, 4,5-dimethyl-N-[(1-ethyl-2-pyrrolidinyl)methyl]-3-methoxythiophene-2-carboxamide fumarate significantly blocks apomorphine induced climbing in mice at a dose of 25 mg/kg intraperitoneally. In rats it blocks a conditioned avoidance response at doses down to 0.8 mg/kg intraperitoneally and also does not cause significant catalepsy below a dose of 50 mg/kg intraperitoneally.

The following compounds as racemic mixtures and in fumarate salt form were especially active in the conditioned avoidance test, with minimum effective doses (mg/kg) as follows:

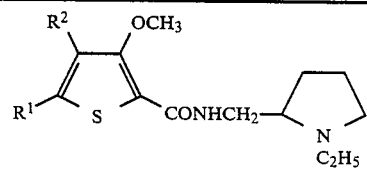

| $R^1$ | $R^2$ | E.D. min. |
|---|---|---|
| 1-pyrazolyl | Cl | 6.25 |
| —(CH$_2$)$_4$— | | 6.25 |
| CH$_3$S | H | 0.78 |
| C$_2$H$_5$S | H | 1.56 |
| (CH$_3$)$_2$CHS | H | 1.56 |
| CH$_3$SO$_2$ | H | 1.56 |
| Cl | Cl | 1.56 |

-continued

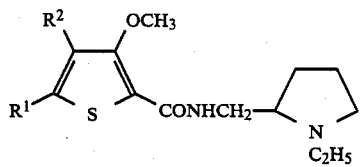

| R¹ | R² | E.D. min. |
| --- | --- | --- |
| CH₃ | H | 3.125 |
| CH₃ | C₂H₅ | 6.25 |
| C₃H₇S | H | 6.25 |
| H | CH₃O | 1.56 |

These tests show that the compounds of the invention block post-synaptic dopamine receptors and are accordingly indicated for the treatment of emesis, depression, anxiety and psychotic conditions such as schizophrenia and acute mania.

The compounds are effective over a wide dosage range, the actual dose administered being dependent on such factors as the particular compound being used, the condition being treated and the type and size of mammal being treated. However, the dosage required will normally fall within the range of 0.05 to 10 mg/kg per day, for example in the treatment of adult humans dosages of from 0.2 to 5 mg/kg may be used.

The compounds and pharmaceutically-acceptable salts of the invention will normally be administered orally or by injection and, for this purpose, said compounds and salts will usually be utilised in the form of a pharmaceutical composition. Such compositions are prepared in a manner well known in the pharmaceutical art and normally comprise at least one active compound or pharmaceutically-acceptable salt of the invention associated with a pharmaceutically-acceptable carrier therefor. Such compositions form part of the present invention. In making such compositions of the present invention, the active ingredient will usually be mixed with a carrier or diluent. Additionally or alternatively it may be enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, stargesh, gum acacia, calcium phosphate, alginates, tragacanth, gelatin, syrup, methyl cellulose, methyl and propylhydroxybenzoate, talc, magnesium stearate or mineral oil. The compositions of the invention may, as is well-known in the art, be formulated so as to provide quick, sustained or delayed release of the active ingredient after administration to the patient.

Depending on the route of administration, the foregoing compositions may be formulated as tablets, capsules or suspensions for oral use or injectable solutions for parenteral use. Preferably the compositions are formulated in a dosage unit form, each dosage containing from 1 to 200 mg more usually 5 to 100 mg, of the active ingredient.

The invention is illustrated by the following Preparations and Examples.

PREPARATION 1

Methyl 4,5-dimethyl-3-hydroxythiophene-2-carboxylate

Dry hydrogen chloride gas was bubbled through a mixture of ethyl 2-methyl-3-oxobutanoate (7.6 g, 50 mmol) and methyl 2-mercaptoacetate (11.2 g, 100 mmol) at −10° C. until saturated. The oil was allowed to stand for 3 hours at room temperature, diluted with dichloromethane and washed with brine. After drying with sodium sulphate and evaporation of solvent the oil was dissolved in methanol (10 ml) and added dropwise to methanolic potassium hydroxide (2N; 75 ml), stirring at room temperature for 1 hour. The solution was diluted with iced water (125 ml) and acidified with 3N hydrochloric acid at −3° to 0° C. to pH1. The precipitate was filtered and washed with water (5.5 g, m.p. 50°–51° C., methanol).

PREPARATION 2

Ethyl 3-hydroxy-5-methylthiophene-2-carboxylate

Dry hydrogen chloride gas was bubbled through a mixture of ethyl acetoacetate (0.2 moles) and ethyl 2-mercaptoacetate (0.4 moles) at −10° C. until saturated. The oil was allowed to stand 4 days at room temperature. Then, 350 ml of 2N ethanolic KOH, was added drop-wise. The resultant mixture was added to 2 liters of ice-water, and acidified with 6M HCl until the pH was approximately 1. The precipitated oil was extracted with benzene, washed with water and dried with sodium sulphate. After removal of solvent the residue was distilled, b.p. 70°–75° C. (0.5 mm).

PREPARATION 3

2-Chloro-2-methoxycarbonylthiophen-3(2H)-one

Sulphuryl chloride (0.11 mol) was added to a stirred solution of methyl 3-hydroxythiophene-2-carboxylate (0.1 mol) (C. Corral, J. Lissavetzty; Syntheses (1984), 847) in anhydrous chloroform (50 ml). After stirring at room temperature for 4 hours the solvent was removed under reduced pressure and the residue used crude in the following preparations (m.p. 70°–71° C., hexane).

PREPARATION 4

Methyl 5-chloro-3-hydroxythiophene-2-carboxylate

A solution of 2-chloro-2-methoxycarbonylthiophene-3(2H)-one (30 mmol) in acetic acid (20 ml) was saturated with dry hydrogen chloride gas. After standing for 3 days the solvent was removed under reduced pressure and the oily residue distilled to give a yellow liquid which crystallised on addition of aqueous acetic acid (m.p. 42°–44° C.).

PREPARATION 5

Methyl 3-hydroxy-5-methylthiophene-2-carboxylate

To a stirred suspension of 2-chloro-2-methoxycarbonylthiophen-3(2H)-one (6.35 g, 33 mmol) in acetic acid (20 ml) was added sulphuric acid (1.8 ml) in acetic acid (20 ml). The mixture was stirred until dissolved then methyl mercaptan was bubbled through for 0.5 hours (total approximately 2 g). The mixture was stirred at room temperature for 18 hours, poured onto ice-water and the oily precipitate extracted into dichloromethane. After evaporation of solvent the crude oil was used in the following preparation.

PREPARATION 6
Methyl 3-hydroxy-5-methylsulphonylthiophene-2-carboxylate

Sodium methane sulphinate (16 mmol) was added to a solution of 2-chloro-2-methoxycarbonylthiophene-3(2H)-one in acetic acid (20 ml) containing sulphuric acid (1.3 ml). After standing for 24 hours the precipitate was filtered, m.p. 138°–140° C. (acetic acid).

PREPARATION 7
Methyl 3-hydroxy-5-(1-pyrazolyl)thiophene-2-carboxylate

Pyrazole (18 mmol) was added to a solution of 2-chloro-2-methoxycarbonylthiophene-3(2H)-one in acetic acid (10 ml). The mixture was allowed to stand at room temperature for 2 days and the precipitate filtered, m.p. 162°–164° C. (acetic acid).

PREPARATION 8
2,4-Dichloro-2-methoxycarbonylthiophen-3(2H)-one

Methyl 3-hydroxythiophene-2-carboxylic acid (60 mmol) and N-chlorosuccinimide (150 mmol) was stirred in acetic acid (40 ml) at 60° C. for 4 hours. The solvent was removed under reduced pressure and residue partitioned between water and benzene. The organic phase was washed with water, dried with sodium sulphate and the solvent removed under reduced pressure to leave an oil which was used in the following reactions.

PREPARATION 9
Methyl 4-chloro-3-hydroxythiophene-2-carboxylate 2,4-Dichloro-2-methoxycarbonylthiophene-3(2H)-one (60 mmol) in acetic acid (50 ml) was treated with metallic zinc (60 mmol) at room temperature for 18 hours. The solvent was removed under reduced pressure and the residue partitioned between water and ether. The organic phase was washed with water, dried with sodium sulphate and the solvent removed under reduced pressure to leave a solid which was crystallised from hexane m.p. 76°–77° C.

PREPARATION 10
Methyl 4,5-dichloro-3-hydroxythiophene-2-carboxylate

Dry hydrogen chloride gas was bubbled into a solution of crude 2,4-dichloro-2-methoxycarbonylthiophen-3(2H)-one (6.8 g, 30 mmol) in acetic acid (30 ml) until saturated. The mixture was allowed to stand for 2 days, concentrated under reduced pressure and the precipitate filtered and recrystallised from methanol, m.p. 107°–108° C.

PREPARATION 11
Methyl 4-chloro-3-hydroxy-5-methoxythiophene-2-carboxylate 2,4-Dichloro-2-methoxycarbonylthiophene-3(2H)-one (10 mmol) was stirred in anhydrous methanol at room temperature for 4 hours and the precipitate filtered, m.p. 109°–111° C. (methanol).

PREPARATION 12
Methyl 5-acetylthio-4-chloro-3-hydroxythiophene-3-carboxylate

To a solution of 2,4-dichloro-2-methoxycarbonylthiophene-3(2H)-one (16 mmol) and concentrated sulphuric acid (0.9 ml) in acetic acid (20 ml) was added thioacetic acid (16 mmol). The mixture was stirred at room temperature for 24 hours and the precipitate filtered, m.p. 133°–135° C. (acetic acid).

PREPARATION 13
Methyl 4-chloro-3-hydroxy-5-mercaptothiophene-2-carboxylate

Methyl 5-acetylthio-4-chloro-3-hydroxythiophene-3-carboxylate (10 mmol) was stirred in 1N NaOH (30 ml). The resulting solution was acidified and the precipitate filtered and recrystallised from hexane, m.p. 48°–49° C.

PREPARATION 14
Methyl 4-chloro-3-methoxy-5-methylthiothiophene-2-carboxylate

To a solution of methyl 4-chloro-3-hydroxy-5-mercaptothiophene-2-carboxylate (10 mmol) in anhydrous acetone (25 ml) was added potassium carbonate (20 mmol) and the mixture stirred for 20 minutes. Dimethyl sulphate (22 mmol) was added and the mixture heated under reflux for 5 hours. The solvent was removed under reduced pressure and the residue partitioned between water and ethyl acetate. The organic phase was washed with water, dried with sodium sulphate and the solvent evaporated. The residue was recrystallised from hexane, m.p. 82°–83° C.

PREPARATION 15
Methyl 4,5-dibromo-3-hydroxythiophene-2-carboxylate

Bromine (0.22 mol) was added to a solution of methyl 3-hydroxythiophene-2-carboxylate (0.1 mol) in acetic acid (40 ml) at room temperature. After the exothermic reaction subsided the mixture was allowed to stand over night, and the mixture concentrated. The precipitate was filtered and recrystallised from methanol, m.p. 128°–130° C.

PREPARATION 16
Methyl 4,5-dimethyl-3-methoxythiophene-2-carboxylate

To a solution of methyl 3-hydroxy-4,5-dimethylthiophene-2-carboxylate (Preparation 1) (29.7 g, 160 mmol) in anhydrous acetone (500 ml) was added anhydrous potassium carbonate (24.5 g, 178 mmol) and the mixture stirred for 1 hour at room temperature. Dimethyl sulphate (22.4 g, 178 mmol) was added and the mixture stirred under reflux for 2.5 hours. The solvent was evaporated under reduced pressure and the residue partitioned between water and ethyl acetate. The organic phase was washed with brine, dried with sodium sulphate and evaporated to give crude product which was used in the following preparation.

PREPARATION 17
3-Methoxy-4,5-dimethylthiophene-2-carboxylic acid

Methyl 4,5-dimethyl-3-methoxythiophene-2-carboxylate (34 g) was heated under reflux in 1M sodium hydroxide solution (500 ml) for 1 hour. After cooling the mixture was acidified with concentrated hydrochloric acid to pH4. The solid was filtered, washed with water and dried, m.p. 142°–143° C.

The following compounds were similarly prepared; intermediates were prepared using the methods outlined in Preparations 1–15 and were carried though without purification except where shown.

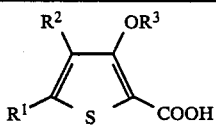

| R$^1$ | R$^2$ | R$^3$ | Melting point °C. |
|---|---|---|---|
| H | H | CH$_3$ | 183 |
| H | H | CH$_2$CH=CH$_2$ | 108–110 |
| CH$_3$ | H | CH$_3$ | 158–160 |
| Cl | H | CH$_3$ | 182–184 |
| CH$_3$S | H | CH$_3$ | 120–123 |
| C$_2$H$_5$S | H | CH$_3$ | 98–101 |
| n-C$_3$H$_7$S | H | CH$_3$ | 81–83 |
| i-C$_3$H$_7$S | H | CH$_3$ | 94–97 |
| C$_6$H$_5$S | H | CH$_3$ | 151 |
| CH$_3$SO$_2$ | H | CH$_3$ | 216–217 |
| C$_6$H$_5$SO$_2$ | H | CH$_3$ | 219 |
| 1-pyrazolyl | H | CH$_3$ | 168–170 |
| 1-(1,2,4-triazolyl) | H | CH$_3$ | 210–211 |
| n-C$_4$H$_9$S | H | CH$_3$ | 100–101 |
| CH$_3$ | C$_2$H$_5$ | CH$_3$ | 144 |
| —(CH$_2$)$_3$— | | CH$_3$ | 171 |
| —(CH$_2$)$_4$— | | CH$_3$ | 146 |
| H | CH$_3$O | CH$_3$ | 128–130 |
| Cl | Cl | CH$_3$ | 175* |
| CH$_3$S | Cl | CH$_3$ | 158 |
| C$_6$H$_5$S | Cl | CH$_3$ | 143–144 |
| 1-pyrazolyl | Cl | CH$_3$ | 180 |
| Br | Br | CH$_3$ | 196–197 |
| CH$_3$ | n-C$_4$H$_9$S | CH$_3$ | 61–62 |
| H | C$_6$H$_5$S | CH$_3$ | 132–133 |
| CH$_3$ | C$_6$H$_5$S | CH$_3$ | 126–127 |

*with decomposition

PREPARATION 18

Resolution of (±)2-aminomethyl-1-ethylpyrrolidine (+)2-aminomethyl-1-ethylpyrrolidine To a solution of L(+) tartaric acid (80 g) in water (150 ml) was added, dropwise (±)2-aminomethyl-1-ethylpyrrolidine keeping the temperature below 20° C. The solution was stirred at room temperature for 1 hour, diluted with ethanol (150 ml) then cooled at 5° C. overnight. The salt was filtered and suspended three times in boiling methanol and filtered whilst warm to give the (+) tartrate (29 g), m.p. 161–162. $(\alpha)_{589}^{25} = +38.8°$ (5% water).

To the above tartrate (29 g) in water (45 ml) was added 30% sodium hydroxide solution (24 ml) and sodium hydroxide pellets (4.5 g), keeping the temperature below 20° C. The solution was extracted with 3×50 ml chloroform. Drying and evaporation of the solvent gave an oil which was distilled b$_{15}$~60° (6.4 g) $(\alpha)_{589}^{25} = +90°$ (5% chloroform).

(−)2-Aminomethyl-1-ethylpyrrolidine was similarly prepared using D(−) tartaric acid as resolving agent. b$_{15}$~62° (9.4 g) $(\alpha)_{589}^{25} = -151°$ (50% chloroform).

EXAMPLE 1

(±)
N-[(1-Ethyl-2-pyrrolidinyl)methyl]-3-methoxy-4,5-dimethylthiophene-2-carboxamide, fumarate To a solution of 3-methoxy-4,5-dimethylthiophene-2-carboxylic acid (18.6 g, 0.1 mol) in dry dichloromethane (250 ml) under nitrogen was added 1,1'-carbonyldiimidazole (16.2 g, 0.1 mol). After stirring for 1 hour (±)2-aminomethyl-1-ethylpyrrolidine (12.8 g, 0.1 mol) was added and the solution stirred at room temperature for 24 hours. The reaction mixture was washed successively with 3×40 ml 3M hydrochloric acid, saturated sodium bicarbonate solution and brine. After drying (sodium sulphate) and evaporation of the solvent the residual oil was dissolved in hot ethyl acetate (750 ml), and fumaric acid (9.3 g) added. The fumarate salt was crystallised from the cooled solution and was filtered, m.p. 123°–125° C.

EXAMPLE 2

(±)
N-[(1-Ethyl-2-pyrrolidinyl)methyl]-3-methoxy-4,5-dimethylthiophene-2-carboxamide, fumarate To a suspension of 3-methoxy-4,5-dimethylthiophene-2-carboxylic acid (1.86 g, 0.010 mol) in dry toluene (30 ml) and two drops of dimethylformamide, thionyl chloride (1.2 g, 0.010 mol) was added drop-wise. The solution was stirred for 15 minutes, the solvent evaporated under vacuum, and a solid was obtained. To a solution of this solid in dry dichloromethane (50 ml) under a nitrogen atmosphere (±)2-aminomethyl-1-ethylpyrrolidine (1.28 g, 0.010 mol) was added. The solution was stirred for 3 hours, the mixture was partitioned between diluted hydrochloric acid and dichloromethane.

The organic layer was washed with sodium bicarbonate solution and brine, dried with sodium sulphate and evaporated. The residue was dissolved in boiling ethylacetate and fumaric acid (0.088 mol) added. After crystallisation, the solid was filtered, m.p. 121°–123° C.

EXAMPLE 3

(−)N-[(1-Ethyl-2-pyrrolidinyl)methyl]-3-methoxy-4,5-dimethylthiophene-2-carboxamide, fumarate Example 1 was repeated using the pure enantiomer (−)2-aminomethyl-1-ethylpyrrolidine. The fumarate salt of the (−) isomer was obtained, m.p. 103°–105° C. (ethyl acetate) $(\alpha)_{589}^{25} = -31.5°$ (1.4% in pyridine).

The following pure enantiomers were similarly prepared:

| R$^1$ | R$^2$ | R$^3$ | enantiomer | melting point °C. | $(\alpha)_{589}^{25}$ |
|---|---|---|---|---|---|
| CH$_3$ | CH$_3$ | CH$_3$ | (+) | 103–105 | +29° |
| CH$_3$S | H | CH$_3$ | (+) | 115–117 | +30.4° |

EXAMPLE 4

N-[(1-Ethyl-2-pyrrolidinyl)methyl]-3-methoxy-5-methylthiophene-2-carboxamide, fumarate To 3-methoxy-5-methylthiophene 2-carboxylic acid (15 mmol) in dichloromethane under nitrogen was added carbonyldiimidazole (15 mmol). The mixture was stirred for three hours, 2-(aminomethyl)-1-ethylpyrrolidine (15 mmol) (commercially available) was added and stirred under nitrogen for 20 hours. The mixture was partitioned between dilute hydrochloric acid and methylene chloride. The acid solution was basified with 2N sodium hydroxide solution and extracted into methylene chloride, washed with water, dried and evaporated.

The residue was dissolved in boiling ethyl acetate, and fumaric acid (11 mmol) added. The mixture was boiled and filtered, m.p. 146°-148° C.

EXAMPLE 5

N-[(1-Ethyl-2-pyrrolidinyl)methyl]-3-methoxy-5-ethyl-thiothiophene-2-carboxamide, fumarate 3-Methoxy-5-ethylthiothiophene 2-carboxylic acid (6 mmol) and carbonyldiimidazole (6 mmol) were stirred under nitrogen in dichloromethane for 3 hours. The amine (6 mmol) was added, and the mixture stirred under nitrogen for 20 hours. The reaction mixture was partitioned between dilute HCl acid and dichloromethane. The organic layer was washed with NaHCO$_3$ solution and water, dried with Na$_2$SO$_4$ and evaporated.

The residue was dissolved in ethyl acetate and 0.58 g of fumaric acid added. The mixture was boiled and filtered, m.p. 124°-127° C.

The following compounds were prepared as fumarate salts and as racemic mixtures according to the methods of Examples 1, 4 and 5.

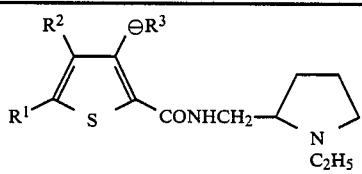

| $R^1$ | $R^2$ | $R^3$ | Melting point °C. |
|---|---|---|---|
| H | H | CH$_3$ | 86 |
| H | H | CH$_2$CH=CH$_2$ | 102-105 |
| Cl | H | CH$_3$ | 160-161 |
| CH$_3$S | H | CH$_3$ | 166 |
| n C$_3$H$_7$S | H | CH$_3$ | 126-128 |
| i C$_3$H$_7$S | H | CH$_3$ | 110-112 |
| C$_6$H$_5$S | H | CH$_3$ | 143 |
| CH$_3$SO$_2$ | H | CH$_3$ | 147-148 |
| C$_6$H$_5$SO$_2$ | H | CH$_3$ | 143 |
| 1-pyrazolyl | H | CH$_3$ | 186 |
| 1-(1,2,4)triazolyl | H | CH$_3$ | 190-192 |
| n-C$_4$H$_9$S | H | CH$_3$ | 107-110 |
| CH$_3$ | C$_2$H$_5$ | CH$_3$ | 96 |
| —(CH$_2$)$_3$— | | CH$_3$ | 160 |
| —(CH$_2$)$_4$— | | CH$_3$ | 107 |
| H | CH$_3$O | CH$_3$ | 133-135 |
| Cl | Cl | CH$_3$ | 134-136 |
| CH$_3$S | Cl | CH$_3$ | 139 |
| C$_6$H$_5$S | Cl | CH$_3$ | 121-123 |
| 1-pyrazolyl | Cl | CH$_3$ | 149-150 |
| Br | Br | CH$_3$ | 120-123 |
| CH$_3$ | n C$_4$H$_9$S | CH$_3$ | 88-90 |
| H | C$_6$H$_5$S | CH$_3$ | 152 |
| CH$_3$ | C$_6$H$_5$S | CH$_3$ | 154-155 |

EXAMPLE 6

N,N-Diethylaminoethyl-3-methoxy-4,5-dimethylthiophene-2-carboxamide, fumarate

To 1,1'-carbonyldi-imidazole (3.26 g, 0.020 mol) in dry tetrahydrofuran (100 ml) under a nitrogen atmosphere was added 4,5-dimethyl-3-methoxythiophene-2-carboxylic acid (3.72 g, 0.020 mol). The solution was stirred for 1 hour and redistilled N,N-diethylethylenediamine (2.9 ml, 0.020 mol) was added. The mixture was stirred for 20 hours then partitioned between 5M hydrochloric acid and ethyl acetate. The aqueous phase was basified with 0.88M aqueous ammonia and extracted into methylene chloride. After drying over anhydrous magnesium sulphate and removal of solvent, the residua oil was dissolved in hot ethyl acetate and fumaric acid (1,78 g) added. The fumarate salt was obtained on cooling, m.p. 108°-110° C. (ethyl acetate).

N,N-dimethylaminoethyl-3-methoxy-4,5-dimethyl-thiophene-2-carboxamide, fumarate was similarly prepared, m.p. 130°-131° (ethyl acetate).

The following Examples illustrate the preparation of typical formulations containing an active ingredient according to the invention.

EXAMPLE 7

Hard gelatin capsule

Each capsule contains
Active ingredient: 10 mg
PEG 4000: 250 mg

The PEG 4000 is melted and mixed with the active ingredient. Whilst still molten the mixture is filled into capsule shells and allowed to cool.

EXAMPLE 8

Tablet

Each tablet contains
Active ingredient: 10 mg
Calcium carbonate: 300 mg
Magnesium stearate: 10 mg
Starch: 30 mg
Hydroxypropylmethylcellulose: 10 mg
Iron oxide: 4 mg The active ingredient is granulated with calcium carbonate and starch. The dried grantulate is blended with lubricant and distinegrant and compressed into tablets of the required dosage strength. The tablet may then be coated.

EXAMPLE 9

Injection

Active ingredient: 10 mg
Water: 1 ml

The active is dissolved in water and distributed into vials, ampoules or pre-pack syringes using appropriate equipment. The product is sterilised.

We claim:

1. A compound of the formula

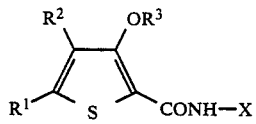

in which $R^1$ and $R^2$ independently are hydrogen, halo, nitro, amino, C$_{2-5}$ acylamino, C$_{1-4}$ alkyl, C$_{1-4}$ alkoxy, C$_{1-4}$ alkylthio, C$_{1-4}$ alkylsulphonyl, imidazolyl attached through a nitrogen atom, pyrazolyl attached through a nitrogen atom, attached through a nitrogen atom, phenyl, phenylthio, phenylsulphonyl or phenylsulphonamido, or phenyl, phenylthio, phenylsulphonyl or phenylsulfonamido substituted with one to three halogen, C$_{1-4}$ alkyl, C$_{1-4}$ alkoxy, hydroxy, nitro, cyano, amino, carboxy or carboxamido groups, or $R^1$ and $R^2$ together form a C$_{3-5}$ alkylene bridge, $R^3$ is C$_{1-4}$ alkyl or C$_{2-4}$ alkenyl, and X is (i) —(CH$_2$)$_n$N(R$^4$)$_2$ where each $R^4$ independently is C$_{1-4}$ alkyl, C$_{2-4}$ alkenyl, C$_6$H$_5$CH$_2$—, or C$_6$H$_5$CH$_2$— substituted with one to three halogen, C$_{1-4}$ alkyl, C$_{1-4}$ alkoxy, hydroxy, nitro, cyano, amino, carboxy or carboxamido groups, and n is 1, 2 or 3, or (ii) an alicyclic group which is

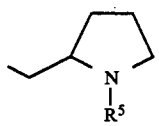

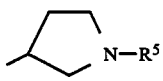

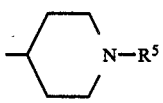

or

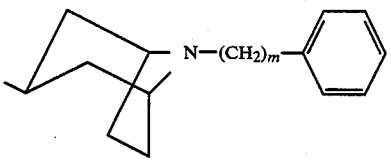

m is 1, 2 or 3 and $R^5$ is $C_{1-4}$ alkyl, $C_{2-4}$ alkenyl, benzyl or benzyl substituted with one to three halogen, $C_{1-4}$ alkyl, $C_{1-4}$ alkoxy, hydroxy, nitro, cyano, amino, carboxy or carboxamido groups; and salts thereof.

2. A compound of claim 1 in which X is an alicyclic group as defined in claim 1; and salts thereof.

3. A compound of claim 2 in which X is

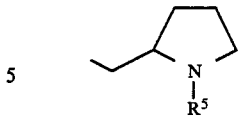

and $R^5$ is $C_{1-4}$ alkyl, $C_{2-4}$ alkenyl or benzyl.

4. A compound according to claim 3 in which $R^5$ is $C_{1-4}$ alkyl.

5. A compound according to claim 4 in which $R^1$ and $R^2$ independently are hydrogen, halo, $C_{1-4}$ alkyl, $C_{1-4}$ alkoxy or $C_{1-4}$ alkylthio and $R^3$ is $C_{1-4}$ alkyl.

6. A compound according to claim 5 in which $R^1$ and $R^2$ are both $C_{1-4}$ alkyl.

7. 4,5-Dimethyl-N-[(1-ethyl-2-pyrrolidinyl)methyl]-3-methoxythiophene-2-carboxamide or a pharmaceutically-acceptable salt thereof.

8. A pharmaceutical formulation comprising a compound according to claim 1 or a pharmaceutically-acceptable salt thereof, together with a pharmaceutically-acceptable diluent or carrier therefor.

9. A pharmaceutical formulation comprising a compound according to claim 3 or a pharmaceutically-acceptable salt thereof, together with a pharmaceutically-acceptable diluent or carrier therefor.

10. A pharmaceutical formulation comprising a compound according to claim 6 or a pharmaceutically-acceptable salt thereof, together with a pharmaceutically-acceptable diluent or carrier therefor.

11. A method of treating in animal, including a human, suffering from or susceptible to a disorder of the central nervous system, which comprises administering an effective amount of a compound as defined in claim 1.

12. A method of treating an animal, including a human, suffering from or susceptible to a disorder of the central nervous system, which comprises administering an effective amount of a compound as defined in claim 6.

13. The compound of claim 1 which is (−)4,5-dimethyl-N-[(1-ethyl-2-pyrrolidinyl)methyl]-3-methoxythiophene-2-carboxamide or a pharmaceutically-acceptable salt thereof.

* * * * *

UNITED STATES PATENT AND TRADEMARK OFFICE
CERTIFICATE OF CORRECTION

PATENT NO.  : 4,904,686

DATED       : February 27, 1990

INVENTOR(S) : Maria I. F. Fernandez, Terrence M. Hotten, and David E. Tupper

It is certified that error appears in the above-identified patent and that said Letters Patent is hereby corrected as shown below:

Column 12, line 58, "nitrogen atom, attached through" should read --nitrogen atom, triazolyl attached through--.

Signed and Sealed this

Second Day of July, 1991

Attest:

HARRY F. MANBECK, JR.

Attesting Officer

Commissioner of Patents and Trademarks